(12) United States Patent
Schwartz et al.

(10) Patent No.: US 6,552,010 B1
(45) Date of Patent: Apr. 22, 2003

(54) TREATMENT OF SLE WITH DEHYDROEPIANDROSTERONE

(75) Inventors: Kenneth E. Schwartz, San Mateo, CA (US); Marc J. Gurwith, Los Altos, CA (US)

(73) Assignee: Genelabs Technologies, Inc., Redwood City, CA (US)

( * ) Notice: Subject to any disclaimer, the term of this patent is extended or adjusted under 35 U.S.C. 154(b) by 0 days.

(21) Appl. No.: 09/710,754

(22) Filed: Nov. 10, 2000

Related U.S. Application Data

(60) Provisional application No. 60/165,108, filed on Nov. 12, 1999.

(51) Int. Cl.[7] ............................................... A61K 31/56
(52) U.S. Cl. ........................ 514/177; 514/170; 514/171
(58) Field of Search .................... 514/170, 171, 514/177

(56) References Cited

U.S. PATENT DOCUMENTS

| | | | |
|---|---|---|---|
| 5,567,696 A | * 10/1996 | McGuire et al. | ............ 514/170 |
| 5,817,650 A | 10/1998 | McGuire et al. | |

FOREIGN PATENT DOCUMENTS

| | | |
|---|---|---|
| WO | WO 94/08589 | 4/1994 |
| WO | WO 00/54763 | 9/2000 |

OTHER PUBLICATIONS

"A double–blind, placebo–controlled, clinical trial of dehydroepiandrosterone in severe systemic lupus erythematosus", van Vollenhoven et al., 1999, 8(3), 181–187.*
Alcocer–Varela et al., *J. Clin. Invest.* 69:1388–1392 (Jun. 1982).
Barrett–Connor et al., *New Engl. J. Med.* 315:1519–1524 (1986).
Bombardier et al., & The Committee on Prognosis Studies in SLE "Derivation of SLEDAI. A disease activity index for lupus patients.," *Arthritis Rheum.* 35:630–640 (Jun. 1992).
Gutierrez–Ramos et al., *Nature* 346:271–274 (Jul. 1990).
Hawker et al., "A reliability study of SLEDAI: a disease activity index for systemic lupus erythematosus," *J. Rheumatol.* 20:4:657–660 (Apr. 1993).
Heinz, D. et al., *Steroids Lip Res.* 5(223):216–223 (1974).
Jungers et al., *Arthritis Rheum.* 25:4:454–457 (Apr. 1982).
Kaki, A.M. and Lewis, G.W., "Inguinal paravascular (lumbar plexus) Neurolytic Block—Description of a Catheter Technique: case report," *Reg. Anesth. Pain. Med.* 23:2:214–218 (Mar.–Apr. 1998).
Krupp, L.B. et al., "The Fatigue Severity Scale: Application to Patients with Multiple Sclerosis and Systemic Lupus Erythematosus" *Arch Neurol.* 46:1121–1123 (1989).
Lahita et al., "Increased Oxidation of Test Osterone in Systemic Lupus Erythematosus" *Arthritis Rheum.* 26:1517 (1983).

Liang et al., "Reliability and Validity of Six Systems for the Clinical Assessment of Disease Activity in Systemic Lupus Erythematosus" *Arthritis Rheum.* 32:9:1107–1118 (1989).
Linker–Israeli et al., *J. Immunol.* 130:6:2651–2655 (Jun. 1983).
Lucas et al., "Prevention of Autoantibody Formation and Prolonged Survival in New Zealand Black/New Zealand White $F_1$ Mice Fed Dehydroisoandrosterone" *J. Clin. Invest.* 75:2091–2093 (Jun. 1985).
Morand et al., "Fibromyalgia syndrome and disease activity in systemic lupus erythematosus," *Lupus* 3:187–191 (Jun. 1994).
Murakawa et al., "Characterization of T Lymphocyte Subpopulations Responsible for Deficient Interleukin 2 Activity in Patients with Systemic Lupus Erythematosus" *J. Immunol.* 134:1:187–195 (Jan. 1985).
Roubinian et al., "Danazol's Failure to Suppress Autoimmunity in NZB/NZW $F_1$ Mice" *Arthritis Rheum.* 22:12:1399–1402 (Dec. 1979).
Shafer et al., "Preoperative anxiety and fear: a comparison of assessements by patients and anesthesia and surgery residents," *Anesth. Analg.* 83:1285–1291 (1996).
Sheean et al., "An open–labelled clinical and electrophysical study of 3,4 diaminopyridine in the treatment of fatigue in multiple sclerosis," *Brain* 121:967–975 (1998).
Singer et al., "Comparison of patient and practioner assessments of pain from commonly performed emergency department procedures," *Ann. Emerg. Med.* 33:6:652–658 (Jun. 1999).
Singer et al., "Determination of the minimal clinically significant difference on a patient visual analog satisfaction scale," *Acad. Emerg. Med.* 5:10:1007–1011 (Oct. 1998).
Steinberg et al., "Approach to the Study of the Role of Sex Hormones in Autoimmunity" *Arthritis Rheum.* 22:11:1170–1176 (Nov. 1979).
Vande Wiele et al., "Studies on the Secretion and Interconversion of the Androgens" *Recent Prog. Horm. Res.* 19:275–310 (1963).
Mease, P.J. (reprint) et al. "GL701 (prasterone, dehydroeplandrosterone) improves systemic lupus erythematosus." Arthritis and Rheumatism, (Sep. 2000) vol. 43, No. 9, Supp. 'SI, pp. 1230–1230. Publisher: Lippincott Williams & Wilkins, 530 Walnut St., Philadelphia, PA 19106–3621. ISSN: 0004–3591., XP001039585.
Database Phin 'Online! Scrip (1999) No. 2493 p20, Nov. 26, 1999 "GeneLabs nears lupus NDA filling" retrieved from STN Database accession No. 1999: 20570 XP002182026 abstract.

(List continued on next page.)

Primary Examiner—Zohreh Fay
Assistant Examiner—Brian-Yong Kwon
(74) Attorney, Agent, or Firm—Emily M. Haliday; Quine Intellectual Property Law Group, P.C.

(57) ABSTRACT

This invention provides a method of treating systemic lupus erythematosus (SLE) with (DHEA) and a related pharmaceutical product.

16 Claims, 1 Drawing Sheet

OTHER PUBLICATIONS

Barry, N. N. et al: "Dehydroeplandrosterone in systemic lupus erythematosus: relationship between dosage, serum levels, and clinical response." Journal of Rheumatology, (Dec. 1998) 25 (12) 2352–6. XP001039566.

Database Phin 'Online! Scrip (1999) No. 2476, p27, Sep. 29, 1999 "Positive results in SLE from Genelabs" retrieved from STN Database accession No. 1999:16620 XP002182027.

Van Vollenhoven R F et al.: Treatment of systemic lupus erythematosus with dehydroepiandrosterone: 50 patients treated up to 12 months. Journal of Rheumatology, (Feb. 1998) 25 (2) 285–9 xp001039567.

Van Vollenhoven R F et al. "Dehydroepiandrosterone in systemic lupus erythematosus. Results of a double–blind, placebo–controlled, randomized clinical trial." Arthritis and Rheumatism, (Dec. 1995) 38 (12) 1826–31, XP001039561.

Database Phin 'Online! Scrip (1997) No. 2228 p20, "Genelab's DHEA ineffective in systemic lupus erythematosus (SLE)" retrieved from STN Database accession No. 97:8552 XP002182028.

Chang, et al: "Solid State Characterization of Dehydroepiandrosterone" Journal of Pharaceutical Sciences. American Pharmaceutical Association. Washington, US, vol. 84, No. 10, 1995, pp. 1169–1179, XP002148232 ISSN:0022–3549.

* cited by examiner

TREATMENT OF SLE WITH DEHYDROEPIANDROSTERONE

CROSS-REFERENCE TO RELATED APPLICATION

This application claims the benefit of U.S. Provisional Application No. 60/165,108 filed Nov. 12, 1999, entitled "Treatment of SLE with Dehydroepiandrosterone" and naming Kenneth Schwartz as the inventor. This prior application is hereby incorporated by reference in its entirety.

FIELD OF THE INVENTION

The field of this invention concerns improvements in the treatment of systemic lupus erythematosus (SLE).

BACKGROUND OF THE INVENTION

REFERENCES

Alcocer-Varela, et al., J. Clin. Invest. 69:1388, (1982).
Barrett-Connor, et al. New Engl. J. Med. 315:1519, (1986).
Gutierrez-Ramos, et al., Nature 346:27, (1990).
Heinz, D., et al., Steroids Lip Res. 5(4):216 (1974).
Jungers, et al., Arthritis Rheum. 25: 454, (1982).
Krupp, L P, et al., Arch Neurol, 46:1121 (1989).
Lahita, et al., Arthritis Rheum 26:1517, (1983).
Liang, et al., Arthritis Rheum 32:1107 (1989).
Linker-Israeli, et.al., J. Immunol. 130:2651, (1983).
Lucas, et al. J. Clin. Invest. 75:2091, (1985).
Murakawy, et al., J. hmmunol 134:187, (1985).
Roubinian, et al., Arthritis Rheum. 22:1399, (1979).
Steinberg, et al., Arthritis Rheum. 22:1170, (1979).
Vande Wiele, et al. Recent Prog. Horm. Res. 19:75, (1963).

SUMMARY OF THE INVENTION

The present invention provides a method for treating systemic lupus erythematosus (SLE). The method entails administering an effective amount of a pharmaceutically active form of DHEA to an individual with SLE, and at least about 4 weeks after initiating DHEA administration, determining the following disease-activity and constitutional-symptom variables characterizing the individual's SLE condition: the SLE Disease activity index (SLEDAI), the Systemic Lupus Activity Measurement (SLAM), the Patient Visual Analog Scale (Patient VAS), and the Krupp Fatigue Severity Score (KFSS). The differences between the values for SLEDAI, KFSS, VAS, and SLAM after initiating DHEA administration and baseline values for SLEDAI, KFSS, VAS, and SLAM before initiating DHEA administration are then determined. A decrease in three of these four variables and either a decrease, no change, or an increase of no more that about 5% of a baseline value in the fourth variable indicates that the individual is responding to said DHEA administration. Preferably, the individual is a human SLE patient, and more preferably a human SLE patient with a SLEDAI value greater than 2.

The DHEA polymorphs known as forms I and II are preferred for use in the treatment method of the invention. Accordingly, in preferred embodiments, at least about 85%, and more preferably at least about 95%, of the DHEA administered is present as the form I polymorph, the form II polymorph, or a combination thereof.

In one embodiment, DHEA is administered at a dose and for a period effective to produce a decrease in three of the four disease-activity and constitutional-symptom variables characterizing an individual's SLE condition and either a decrease, no change, or an increase of no more that about 3% of a pretreatment baseline value in the fourth variable. In another embodiment, DHEA is administered at a dose effective to reduce the risk of an SLE flare at about 200 days of DHEA administration by at least about 5%. Preferably, the method entails administering a daily oral dose of at least about 100 mg, and more preferably about 200 mg, of a pharmaceutically active DHEA. In one embodiment, DHEA administration is continued for a period of at least about 40 weeks.

One advantage of the treatment method of the invention is that is can be combined with other therapies. For example, the treatment method can be carried out with an SLE patient receiving an orally administered drug, such as a glucocorticoid, a non-steroidal anti-inflammatory agent, an immunosuppressant, or an anti-malarial drug. In this case, the treatment method includes continuing administration of the drug during the period of DHEA administration.

The invention also provides a pharmaceutical product for use in treating systemic lupus erythematosus (SLE) in an individual. The pharmaceutical product includes a plurality of doses of a pharmaceutically active form of DHEA, and instructions for performing the treatment method of the invention.

The invention includes the use of the pharmaceutical product of the invention, for treating systemic lupus erythematosus (SLE) in a human patient.

Another aspect of the invention is the use of a pharmaceutically active acid, salt, or ester form dehydroepiandrosterone (DHEA) in the preparation of a tablet-form medicament for use in treating systemic lupus erythematosus (SLE) in a human patient, with a greater than 50% expectation of achieving improvement in the measured values of at least three of the disease-activity and constitutional-symptom variables characterizing a patient's SLE condition consisting of SLEDAI, KFSS, VAS, and SLAM, and an increase of no greater than 5% of a pretreatment baseline value in the fourth variable, where the change in each variable is determined from the difference between a pretreatment baseline value and values during treatment, when the patient has a pre-treatment SLEDAI value greater than 2, and is treated with a dose of at least about 100 mg per day DHEA, administered orally. In a preferred variation of this embodiment, the patient is treated with a dose of at least about 200 mg DHEA per day for a period of at least about 40 weeks.

BRIEF DESCRIPTION OF THE DRAWING

FIG. 1 shows a graph of the percentage of patients surviving without a flare over the indicated duration of the study.

DETAILED DESCRIPTION

Figure 1:
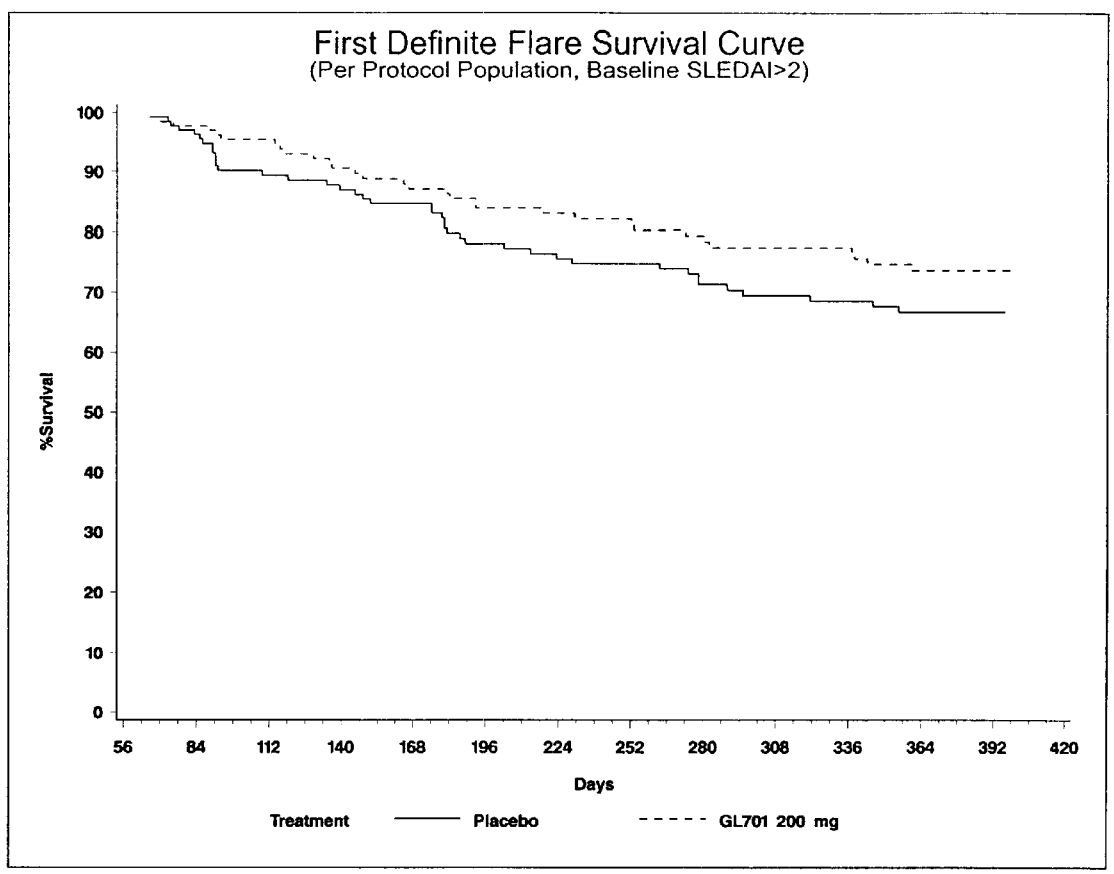
FIG. 1 shows the results of a clinical trial conducted to determine the effect of DHEA treatment on SLE flares, which is described below in connection with Tables 6-8. Patients received 200 mg DHEA per day, administered orally in capsule form, or with a non-drug capsule (placebo).

The present invention relates to the treatment of systemic lupus erythematosus (SLE) with dehydroepiandrosterone (DHEA). In preferred embodiments, the method employs four SLE evaluation criteria: the SLE Disease activity index (SLEDAI), the Systemic Lupus Activity Measurement (SLAM), the Patient Visual Analog Scale (Patient VAS), and the Krupp Fatigue Severity Score (KFSS). Preferably, individuals with a SLEDAI value greater than 2.0 are selected for DHEA treatment. In addition, the treatment method entails comparing the values for these disease-activity and constituitional-symptom variables before and after initiating DHEA administration as an indication of response to DHEA administration.

I. SLE Evaluation Criteria

A. The SLE Disease Activity Index

The SLEDAI (SLE Disease Activity Index) was developed as a clinical index for the measurement of disease activity (Bombardier). It consists of a weighted index of 24 questions covering 9 organ systems for disease activity in SLE. Table 1 shows the SLEDAI questionaire employed in the present study. As seen, the SLEDAI score is weighted, with 8 points being assigned for central nervous system and vascular, 4 points for renal and muscloskeletal, 2 points for serosal, dermal, and immunologic, and 1 point for constitutional and hematologic findings. Each system is rated as present or absent over the ten day period before and including the day of evaluation. Thus, SLEDAI, as a quantitative measure of SLE disease activity, assesses only recent disease activity, which must be present within the previous 10 days as an indication of current disease state.

B. The Systemic Lupus Activity Measurement

The SLAM (Systemic Lupus Activity Measurement) covers symptoms that occurred during the previous month and includes 24 clinical manifestations and 8 laboratory parameters (Liang). Clinical and laboratory parameters are scored for both activity and severity. A manifestation or symptom is determined to be either active or not active; severity is then used to expand a scale's graduations and is "judged by the need to treat with immunosuppressive agents, the need to follow the patient more closely, or the functional or prognostic consequences of the manifestations" (Liang). Table 2 below shows the SLAM questionaire used in the present study. The theoretical range for SLAM is 0 to 86, with scores in SLE patients typically falling in the range of 5 to 20.

C. The Patient Visual Analog Scale

In determining Patient VAS (Patient Visual Analog Scale), patient overall (or "global") assessment is based on a visual analog scale, with a range from "no problems at all" (0) to "the worst I have ever felt" (100). The scale is shown at the bottom (question 2) in Table 3. The patient is asked to mark on the scale how they have felt the past week. The distance in mm's from "0" is measured to arrive at the score.

D. The Krupp Fatigue Severity Score

The KFSS (Krupp Fatigue Severity Score) is a composite score based on the mean of 9 questions, with a possible range from 1-7, where higher scores indicate greater fatigue (Krupp), as shown at the top (question 1) in Table 3. The theoretical range of KFSS is 0 to 7, with scores ranging typically in SLE patients between 4 and 7.

E. Changes in Evaluation Criteria Values

For all four variables, an increase in the measured or determined value represents a more severe condition or assessment, and a decrease in the value represents an improvement in the condition or assessment.

For each of the disease activity variables (SLEDAI and SLAM) and constitutional symptom variables (Patient VAS and KFSS), the value of interest for each patient is determined as the difference between a pretreatment baseline value, calculated as the mean of two baseline values, taken prior to any treatment with DHEA), and values taken during treatment, calculated as the mean of all values obtained during on-treatment scheduled visits, e.g., 13, 26, 39, and 52 weeks of treatment.

For each of the variables, an improvement in the variable is defined as either (i) no change in the variable or (ii) a decrease in the variable. Thus, for example, an improvement in a baseline SLEDAI score of 5.00 would be any value 5.00 or less. A change in a variable that represents a worsening of the state or condition is any increase in the measured value.

A successful responder in the clinical trial studies that were carried out, in accordance with the invention, is defined as a patient that shows an improvement in three of the four variables (that is, SLEDAI, SLAM, Patient VAS, and KFSS) and an increase in the fourth variable that is no greater than 5% of the pretreatment baseline value. Thus, for a baseline SLEDAI value of 5.0, and a 3% cap, the maximum allowed increase in SLEDAI value, for classification as a 3% responder is 0.15

TABLE 1

SLEDAI SCORE

VISIT: ☐ Screening ☐ Qualifying ☐ 1 ☐ 2 ☐ 3 ☐ Completion/Early Termination ☐ Other
WEEK: (0) (13) (26) (39) (52)

Check box: If descriptor is present at the time of visit or in the preceding 10 days.

| Wt. | Present | Descriptor | Definition |
|---|---|---|---|
| 8 | ☐ | Seizure | Recent onset. Exclude Metabotic, infectious or drug cause. |
| 8 | ☐ | Psychosis | Altered ability to function in normal activity due to severe disturbance in the perception of reality. Include hallucinations, incoherence. marked loose associations, impoverished thought content, marked illogical thinking, bizarre, disorganized, or catatonic behavior. Exclude uremia and drug causes. |
| 8 | ☐ | Organic Brain Syndrome | Altered mental function with impaired orientation, memory or other intellectual function, with rapid onset and fluctuating clinical features. Include clouding of consciousness with reduced capacity to focus, and inability to sustain attention to environment, plus at least two of the following: perceptual disturbance, incoherent speech, insomnia or daytime drowsiness, or increased or decreased psychomotor activity. Exclude metabotic, infectious or drug causes. |
| 8 | ☐ | Visual Disturbance | Retinal changes of SLE. Include cytoid bodies, retinal hemorrhages. serous exudate or hemorrhages in the choroid, or optic neuritis. Exclude hypertension. infection, or drug causes. |
| 8 | ☐ | Cranial Nerve Disorder | New onset of sensory or motor neuropathy involving cranial nerves. |

TABLE 1-continued

SLEDAI SCORE

VISIT: ☐ Screening ☐ Qualifying ☐ 1 ☐ 2 ☐ 3 ☐ Completion/Early Termination ☐ Other
WEEK: (0) (13) (26) (39) (52)

Check box: If descriptor is present at the time of visit or in the preceding 10 days.

| Wt. | Present | Descriptor | Definition |
|---|---|---|---|
| 8 | ☐ | Lupus Headache | Severe persistent headache; may be migrainous, but must be non-responsive to narcotic analgesia. |
| 8 | ☐ | CVA | New onset of cerebrovascular accident(s). Exclude arteriosclerosis. |
| 8 | ☐ | Vasculitis | Ulceration, gangrene, tender finger nodules, periungual infarction. splinter hemorrhages, or biopsy or angiogram proof of vasculitis. |
| 4 | ☐ | Arthritis | More than 2 joints with pain and signs of inflammation (i.e. tenderness, swelling, or effusion). |
| 4 | ☐ | Myositis | Proximal muscle aching/weakness, associated with elevated creatine phosphokinase/adolase or electromyogram changes or a biopsy showing myositis. |
| 4 | ☐ | Urinary Casts | Heme-granular or red blood cell casts. |
| 4 | ☐ | Hematuria | >5 red blood cells/high power field. Exclude stone, infection or other cause. |
| 4 | ☐ | Proteinuria | >0.5 gm/24 hours. New onset or recent increase of more than 0.5 gm/24 hours. |
| 4 | ☐ | Pyuria | >5 white blood cells/high power field. Exclude infection. |
| 2 | ☐ | New Rash | New onset or recurrence of inflammatory type rash. |
| 2 | ☐ | Alopecia | New onset or recurrence of abnormal, patchy or diffuse toss of hair. |
| 2 | ☐ | Mucosal ulcers | New onset or recurrence of oral or nasal ulcerations. |
| 2 | ☐ | Pleurisy | Pleuritic chest pain with pleural rub or effusion, or pleural thickening. |
| 2 | ☐ | Pericarditis | Pericardial pain with at least 1 of the following: rub, effusion, or electrocardiogram confirmation. |
| 2 | ☐ | Low complement | Decrease in CH50. C3, or C4 betow the lower limit of normal for testing laboratory |
| 2 | ☐ | Increased DNA binding | >25% binding by Farr assay or above normal range for testing laboratory. |
| 1 | ☐ | Fever | >38° C. Exclude infectious cause. |
| 1 | ☐ | Thrombocytopenia | <100,000 platelets/mm$^3$. |
| 1 | ☐ | Leukopenia | <3,000 White blood cells/mm$^3$. Exclude drug causes. |
| ___ | | TOTAL SCORE | (Sum of weights next to descriptors marked present) |

TABLE 2

SLAM ASSESSMENT

VISIT: ☐ Screening ☐ Qualifying ☐ 1 ☐ 2 ☐ 3 ☐ Completion/Early Termination ☐ Other
WEEK: (0) (13) (26) (39) (52)

| Constitutional | ABSENT or NORMAL | MILD/ MODERATE | | SEVERE | NOT RECORDED |
|---|---|---|---|---|---|
| 1. Weight Loss | ☐ 0 | ☐ 1 <br> <10% body weight | | ☐ 3 <br> >10% | ☐ |
| 2. Fatigue | ☐ 0 | ☐ 1 <br> No limits on activity | | ☐ 3 <br> Functional limitation | ☐ |
| 3. Fever | ☐ 0 | ☐ 1 <br> 37.5–38.5° C. | | ☐ 3 <br> >38.5° C. | ☐ |

| Integument | ABSENT | MILD | MODERATE | SEVERE | NOT RECORDED |
|---|---|---|---|---|---|
| 4. Oral/nasal ulcers, or periungal erythema, malar rash, photosensitive rash, or nail fold infarct | ☐ 0 | ☐ 1 <br> Present | | | ☐ |
| 5. Alopecia | ☐ 0 | ☐ 1 | ☐ 2 | | ☐ |

TABLE 2-continued

SLAM ASSESSMENT

VISIT: ☐ Screening ☐ Qualifying ☐ 1 ☐ 2 ☐ 3 ☐ Completion/Early Termination ☐ Other
WEEK: (0) (13) (26) (39) (52)

| | | | | | |
|---|---|---|---|---|---|
| | | Hair loss with trauma | Spontaneous hair loss | | |
| 6. Erythematous, maculopapular rash, discoid lupus, lupus profundus, or bullous lesions | [0] | [1]<br><20% total body surface (TBA) | [2]<br>20–50% TBA | [3]<br>>50% TBA | ☐ |
| 7. Vasculitis (leucocytociastic vasculitis, urticaria, paplpable purpura, livedo reticularis, ulcer or pannicutitis | [0] | [1]<br><20% (TBA) | [2]<br>20–50% TBA | [3]<br>>50% TBA or necrosis | ☐ |

| Eye | ABSENT | MILD | MODERATE | SEVERE | NOT RECORDED |
|---|---|---|---|---|---|
| 8. Cytoid bodies | [0] | [1]<br>Present | | [3]<br>Visual acuity <20/200 | ☐ |
| 9. Hemorrhage (retinal or choroidal) or episcleritis | [0] | [1]<br>Present | | [3]<br>Visual acuity <20/200 | ☐ |
| 10. Papillitis or pseudotumor cerebri | [0] | [1]<br>Present | | [3]<br>Visual acuity <20/200 | ☐ |

| Reticuloendothelial | ABSENT or NORMAL | MILD | MODERATE | SEVERE | NOT RECORDED |
|---|---|---|---|---|---|
| 11. Diffuse lymphadenopathy (cervical, axillary, epitrochlear) | [0] | [1]<br>Shotty | [2]<br>>1 cm × 1.5 cm | | ☐ |
| 12. Hepato - or splenomegaly | [0] | [1]<br>Palpabte only with inspiration | [2]<br>Palpable without inspiration | | ☐ |

| Pulmonary | ABSENT or NORMAL | MILD | MODERATE | SEVERE | NOT RECORDED |
|---|---|---|---|---|---|
| 13. Pleural effusion/pleurisy | [0] | [1]<br>Shortness of breath or pain only with prompting. exam normal or near normal | [2]<br>Shortness of breath or pain with exercise, decreased breath sounds and dull lower lobe(s) | [3]<br>Shortness of breath or pain at rest, decreased breath sounds and dull middle and lower lobe(s) | ☐ |
| 14. Pneumonitis | [0] | [1]<br>X-ray infiltrates only | [2]<br>Shortness of breath with exercise | [3]<br>Shortness of breath at rest | ☐ |

| Cardiovascular | ABSENT or NORMAL | MILD | MODERATE | SEVERE | NOT RECORDED |
|---|---|---|---|---|---|
| 15. Raynaud's | [0] | [1]<br>Present | | | ☐ |
| 16. Hypertension | [0] | [1]<br>Diast. 90–105 | [2]<br>Diast. 105–115 | [3]<br>Diast. > 115 | ☐ |
| 17. Carditis | [0] | [1] | [2] | [3] | ☐ |

TABLE 2-continued

SLAM ASSESSMENT

VISIT: ☐ Screening ☐ Qualifying ☐ 1 ☐ 2 ☐ 3 ☐ Completion/Early Termination ☐ Other
WEEK: (0) (13) (26) (39) (52)

| | | Pericarditis by EKG &/or RUB &/or effusion by echo. no sx | Chest pain or arrhythmia | Myocarditis with hemodynamic compromise &/or arrhythmia | |
|---|---|---|---|---|---|
| Gastrointestinal | ABSENT or NORMAL | MILD | MODERATE | SEVERE | NOT RECORDED |
| 18. Abdominal pain (Serositis, pancreatitis, ischemic bowel, etc.) | ☐ 0 | ☐ 1 Complaint | ☐ 2 Limiting pain | ☐ 3 Paritoneal signs/ascites | ☐ |
| Neuromotor | ABSENT or NORMAL | MILD | MODERATE | SEVERE | NOT RECORDED |
| 19. Stroke syndrome (includes mononeuritis multiplex, transient ischemic attack (TIA). reversible ischemic neurologic deficit (RIND) cerebravascular accident (CVA) retinal vascular thrombosis) | ☐ 0 | ☐ 1 Single TIA | ☐ 2 Multiple TIA/RIND or mononeuritis multiplex or cranial neuropathy and chorea | ☐ 3 CVA/myelitis, retinal vascular occlusion | ☐ |
| 20. Seizure | ☐ 0 | ☐ 1 1–2/month | ☐ 2 >2/month | ☐ 3 Status epitepticus | ☐ |
| 21. Cortical dysfunction | ☐ 0 | ☐ 1 Mild depression/ personality disorder or deficit | ☐ 2 Δ in sensorium, severe depression, or limiting cognitive impairment | ☐ 3 Psychosis, dementia. or coma | ☐ |
| 22 Headache (including migraine equivalents) | ☐ 0 | ☐ 1 Symptoms or transient neuro deficit | ☐ 2 interteres somewhat with normal activities | ☐ 3 Incapacitating/ aaceptic meningitis | ☐ |
| 23. Myalgia/myositis | ☐ 0 | ☐ 1 Complaint | ☐ 2 Limits some activity | ☐ 3 Incapacitating | ☐ |
| Joints | ABSENT or NORMAL | MILD | MODERATE | SEVERE | NOT RECORDED |
| 24. Joint pain from synovitis and/or fenosynovitis | ☐ 0 | ☐ 1 Arthafgia only | ☐ 2 Objective inflammation | ☐ 3 Limited function | ☐ |
| Laboratory | NORMAL | MILD | MODERATE | SEVERE | UNKNOWN NOT RECORDED |
| 25. Hematocrit | ☐ 0 >35 | ☐ 1 30–35 | ☐ 2 25–29.9 | ☐ 3 <25 | ☐ |
| 26. WBC | ☐ 0 >3500 | ☐ 1 3500–2000 | ☐ 2 2000–1000 | ☐ 3 <1000 | ☐ |
| 27. Lymphocyte count | ☐ 0 1500–4000 | ☐ 1 1499–1000 | ☐ 2 999–500 | ☐ 3 <499 | ☐ |
| 26. Platelet count | ☐ 0 >150T | ☐ 1 100–150T | ☐ 2 99–50T | ☐ 3 <50T | ☐ |
| 29. ESR (westergren) | ☐ 0 <25 | ☐ 1 25–50 | ☐ 2 51–75 | ☐ 3 >75 | ☐ |

TABLE 2-continued

SLAM ASSESSMENT

VISIT: ☐ Screening ☐ Qualifying ☐ 1 ☐ 2 ☐ 3 ☐ Completion/Early Termination ☐ Other
WEEK: (0)   (13) (26) (39) (52)

| | | | | | |
|---|---|---|---|---|---|
| 30. Serum creatine or creatine clearance | [0] 0.5–1.3 mg/dl or 80–100% CrCt | [1] 1.4 · 2 mg/dl or 79–60% CrCt | [2] 2.1–4 mg/dl or 30–60% CrCt | [3] >4 mg/dl or <30% CrCt | ☐ |
| 31. Urine sediment | [0] Urine protein ≦150 mg/24 hours | [1] >5 RBC &/or WBC/hpf &/or 0 to 1–3 granular &/or cellular casts/ hpt &/or 1–2t proteinuria &/or <500 mg/L 24" urine protein | [2] >10 RBC &/or WBC/hpt &/or >3 granular &/or cellular cast/hpf &/or 3 or 4+ &/or 500 mg/L-3.5 g/L 24" urine protein | [3] >25 RBC or WBC/hpf &/or Red cell cast &/or >4+ proteinuria &/or >3.5 g/L 24" urine protein | ☐ |

TABLE 3

PATIENT SELF-ASSESSMENT QUESTIONNAIRE

VISIT: ☐ Screening ☐ Qualifying ☐ 1 ☐ 2 ☐ 3 ☐ Completion/Early Termination ☐ Other
WEEK: (0)   (13) (26) (39) (52)

SELF-ADMINISTERED BY THE PATIENT: We are interested in learning whether or not you are affected by fatigue because of your illness, as well as the overall effects of your illness on your general well-being.
1) Circle a number between 1 and 7 that indicates your degree of agreement with each of the statements below for the past week, where 1 indicates that you strongly disagree and 7 means that you strongly agree.

|   |   | DISAGREE |   |   |   |   |   | AGREE |
|---|---|---|---|---|---|---|---|---|
| a) | My motivation is lower when I am fatigued. | 1 | 2 | 3 | 4 | 5 | 6 | 7 |
| b) | Exercise brings on my fatigue. | 1 | 2 | 3 | 4 | 5 | 6 | 7 |
| c) | I am easily fatigued. | 1 | 2 | 3 | 4 | 5 | 6 | 7 |
| d) | Fatigue interferes with my physical functioning. | 1 | 2 | 3 | 4 | 5 | 6 | 7 |
| e) | Fatigue causes frequent problems for me. | 1 | 2 | 3 | 4 | 5 | 6 | 7 |
| f) | My fatigue prevents sustained physical functioning. | 1 | 2 | 3 | 4 | 5 | 6 | 7 |
| g) | Fatigue interferes with carrying out certain duties and responsibilities. | 1 | 2 | 3 | 4 | 5 | 6 | 7 |
| h) | Fatigue is among my three most disabling symptoms. | 1 | 2 | 3 | 4 | 5 | 6 | 7 |
| i) | Fatigue interferes with my work, family or social life. | 1 | 2 | 3 | 4 | 5 | 6 | 7 |

2) Please indicate on the scale below, using a vertical line, how you have felt in the past week (including psychological and physical factors).

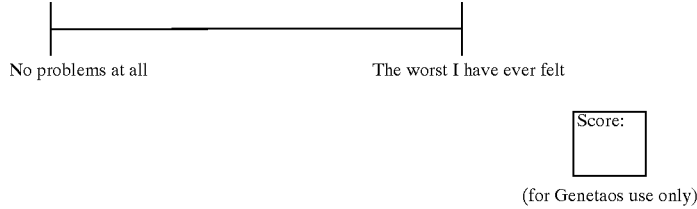

No problems at all                The worst I have ever felt

Score: ☐

(for Genetaos use only)

II. Clinical-Trial Data
A. Effect of DHEA Treatment on SLEDAI, SLAMS Patient VAS, and KFSS Table 4 shows baseline characteristics of two patient groups employed in a clinical trial study, a 176-patient placebo group and a 170-patient treatment group. As seen, the two groups are comparable for all characteristics that were determined, including mean baseline SLEDAI, SLAM, Patient and Physician VAS, and fatigue score. The mean baseline scores represent the mean of two value determinations made prior to treatment.

TABLE 4

| | Baseline Comparability (Per-protocol population) | |
|---|---|---|
| Variable | Placebo (N = 176) | GL701 (N = 170) |
| Menopausal | 86 (49%) | 74 (44%) |
| Prednisone use | 98 (56%) | 91 (54%) |
| SLEDAI total > 2 | 133 (76%) | 132 (78%) |

TABLE 4-continued

Baseline Comparability
(Per-protocol population)

| Variable | Placebo (N = 176) | GL701 (N = 170) |
|---|---|---|
| Race (white) | 125 (71%) | 132 (78%) |
| Smoking now | 25 (14%) | 32 (18%) |
| Age at screening (sd) | 43.8 (10.5) | 44.1 (11.1) |
| SLEDAI total (sd) | 5.9 (4.4) | 6.5 (4.3) |
| SLAM (sd) | 12.0 (2.9) | 12.3 (2.8) |
| Patient VAS (sd) | 55.1 (18.8) | 55.2 (18.6) |
| Physician VAS (sd) | 30.6 (13.5) | 30.4 (13.2) |
| Fatigue score (sd) | 5.6 (1.2) | 5.5 (1.2) |
| SLICC Score (sd) | 1.3 (1.5) | 1.2 (1.5) |
| SF36-Mental (sd)* | 42.1 (11.8) | 43.3 (10.4) |
| SF36-Physical (sd)* | 31.3 (8.4) | 31.5 (8.4) |

N = 174 and N = 169 for placebo and GL170 groups, respectively

Each group, in turn, can be broken down into three subgroups: (I) total patient population (II) all patients with SLEDAI values greater than 2, and (III) patients having SLEDAI values greater than 2 and currently being treated with prednisone (at dose greater than 2 mg/prednisone /day), where the number of patients in each subgroup is indicated by N in the Table 5.

Table 5 shows the results of a clinical-trial in which the three placebo and three treatment subgroups were treated with DHEA over an extended period. Treatment was with 200 mg DHEA per day, administered orally in capsule form, or with a non-drug capsule (placebo). Mean duration of the treatment for each group was somewhat higher for the placebo group (308 days for placebo vs 288.4 days for DHEA, but median durations were almost the identical (362 vs. 359 days, respectively.).

The three columns in the table represent total of the three subgroups for both the placebo and treatment group. The three rows represent responders in which an improvement (no change or decrease in value) in three the three of the four variables was observed and an increase in the fourth variable of no more than 3% (first row), 5% (second row), and 10% (third row) of the pretreatment baseline value.

As seen, patients in the treatment subgroups II (SLEDAI values greater than 2) and III (SLEDAI values greater than 2 and daily prednisone treatment) showed a greater than 50% responder rate, as defined by either a 3%, 5%, or 10% "increase" in the fourth variable, compared with a responder rates substantially less than 50% for the same two placebo subgroups.

Thus, in accordance with one aspect of the invention, the responder rate in DHEA treatment can be substantially improved, in both treatment by DHEA alone, or in combination with a second anti-SLE drug, such as prednisone, by (i) prescreening SLE patients for SLEDAI value, (ii) selecting for DHEA treatment, those patients with a SLEDAI value greater than 2.0, and (iii) treating the selected patient with a daily oral dose of DHEA.

In particular, this method can be practiced with a greater than 50% expectation of achieving improvement in the measured values of at least three of the disease-activity and constitutional-symptom variables characterizing a patient's SLE condition consisting of SLEDAI, KFSS, VAS, and SLAM, with an increase of no more than a 5% of a pretreatment baseline value in the fourth variable, where the changes in each variable are determined from the difference between a pretreatment baseline value and the mean of all values obtained at regularly scheduled intervals during treatment.

B. Effect of DHEA Treatment on SLE Flares

A clinical trial was conducted to determine the effect of DHEA treatment on SLE flares. An SLE flare is a significant new clinical manifestation of the disease (i.e., one that was not previously present in the patient or not previously as severe) and/or a clinical intervention. Table 6 identifies the clinical findings or interventions that were scored as flares in the present study. Any patient having at least one of these finding or interventions was scored as having a flare.

TABLE 6

SLE FLARES

| Type of Clinical Finding/ Intervention | Definition of a Flare |
|---|---|
| New/worse CNS Lupus | Scored on SLEDAI & not present on previous visit. |

TABLE 5

Window Analyses (3%, 5%, and 10%)

| | Group I: All patients | | | Group II: All patients with SLEDAI > 2 | | | Group III: All patients with SLEDAI > 2, Pred > 0 | | |
|---|---|---|---|---|---|---|---|---|---|
| Variable | Placebo (N = 176) | GL701 (N = 170) | P value Improvement | Placebo (N = 133) | GL701 (N = 132) | P value Improvement | Placebo (N = 80) | GL701 (N = 73) | P value Improvement |
| Responders (3% window)* | 57 32.4% | 77 45.3% | **P = 0.014 39.8% | 47 35.3% | 72 54.5% | P = 0.002 54.4% | 26 32.5% | 39 53.4% | P = 0.010 64.3% |
| Responders (5% window)* | 62 35.2% | 79 46.5% | **P = 0.034 32.1% | 50 37.6% | 73 55.3% | P = 0.004 47.1% | 26 32.5% | 40 54.8% | P = 0.006 68.6% |
| Responders (10% window)* | 69 39.2% | 92 54.1% | **P = 0.006 38.0% | 56 42.1% | 84 63.6% | P = 0.001 51.1% | 27 33.8% | 45 61.6% | P = 0.001 82.2% |

*baseline mean + 3%, 5%, or 10% of patients baseline mean
**P value not valid due to statistically significant treatment by SLEDAI interaction

TABLE 6-continued

SLE FLARES

| Type of Clinical Finding/ Intervention | Definition of a Flare |
|---|---|
| Vasculitis | Scored on SLEDAI & not present on previous visit. |
| Myositis | Scored on SLEDAI & not present on previous visit. |
| Hematologic | Platelets < 60,000 or hemoglobin < 7 mg/dL or decrease of at least 3 mg/dL. |
| Nephritis | Proteinuria with pyuria and/or hematuria treated with new/increased dose of corticosteroids or immunosuppressives. |
| Steroids | An increase of ≧ 2.5 mg for at least 7 days for SLE related reasons. |
| Immunosuppressives or anti-malarials | New use of or increase in dose for at least 7 days for SLE related reasons. |
| Hospitalization | Hospitalization for new SLE manifestation |

Table 7 shows baseline characteristics of two patient groups employed in a clinical trial study including a 109-patient placebo group and a 189-patient treatment group. As seen, the two groups are comparable for all characteristics that were determined, including mean baseline SLEDAI, SLAM, Patient VAS (indicated as "Patient Global Assessment Score"), and KFSS. (This table shows the group mean baseline scores determined prior to treatment.)

TABLE 7

BASELINE CHARACTERISTICS OF FEMALE SLE PATIENTS BY TREATMENT GROUP

|  | PLACEBO (N = 192)* | DHEA (N = 189)* |
|---|---|---|
| Mean Age (yrs) | 43.8 | 44.4 |
| Caucasian (yes) | 71.4% | 77.2% |
| Post-Menopausal (yes) | 47.9% | 43.9% |
| Mean (Median) Prednisone Dose | 3.7 (2.5) mg/d | 3.5 (3.8) mg/d |
| Prednisone Use at Baseline (yes) | 53.7% | 54.5% |
| Immunosuppressive Use at Baseline (yes) | 14.6% | 16.9% |
| Anti-Malarial Use at Baseline (yes) | 25.0% | 23.3% |
| Mean (Median) SLEDAI† Score | 5.8 (5.0) | 6.5 (6.0) |
| Mean (Median) SLAM‡ Score | 12.0 (12.0) | 12.2 (12.0) |
| Mean (Median) Patient global assessment§ Score | 55.4 (57.0) | 55.2 (57.0) |
| Mean (Median) KFSS§ Score | 5.6 (5.7) | 5.5 (5.9) |
| Mean (Median) DHEA-S ‖ | 103 (50) μg/dl | 107 (61) μg/dl |
| Mean (Median) C3 Complement | 103.0 (102.0) mg/dl | 102.8 (100.0) mg/dl |
| Mean (Median) C4 Complement | 18.0 (16.0) mg/dl | 17.9 (17.0) mg/dl |
| Mean (Median) Double-Stranded DNA Antibody | 24.4 (1.9) IU/dl | 34.8 (2.6) IU/dl |

*Baseline values were not obtained on all patients for some clinical laboratory tests. For DHEA-S, N = 163, placebo, and N = 165, DHEA. For C3, C4 and double-stranded DNA antibody, N = 178, placebo, and N = 169, DHEA.
†Systemic Lupus Erythematosus Disease Activity Index
‡Systemic Lupus Activity Measure

TABLE 7-continued

BASELINE CHARACTERISTICS OF FEMALE SLE PATIENTS BY TREATMENT GROUP

|  | PLACEBO (N = 192)* | DHEA (N = 189)* |
|---|---|---|

§Krupp Fatigue Severity Scale
‖ Dehydroepiandrosterone sulfate
To convert DHEA-S to μmol/liter, multiply by 0.027. To convert C3 and C4 complement to g/liter, multiply by 0.01.

Clinical trial results were analyzed for each group (placebo and DHEA-treated) as a whole ("per-protocol"), as well as broken down into three subgroups: all patients with SLEDAI values greater than 2 ("active SLE"), and patients having SLEDAI values greater than 2 and receiving corticosteroids and/or immunosuppressives ("more severe SLE").

Table 8 shows the results of a clinical-trial in which the patients were treated with DHEA or placebo over an extended period. Patients received 200 mg DHEA per day, administered orally in capsule form, or with a non-drug capsule (placebo). Mean duration of the treatment for each group was somewhat higher for the placebo group (308.4 days for placebo vs 288.4 days for DHEA, but median durations were almost the identical (362 vs. 359 days, respectively.).

The first column of the table shows the patient population or sub-population analyzed, the next three columns show the results of the study for patients identified as responders according to the following criteria: (1) Weighted average change from baseline for Systemic Lupus Activity Measure (SLAM)<1; for Systemic Lupus Erythematosus Disease Activity Index (SLEDAI)<0.5; for Krupp Fatigue Severity Scale (KFSS)<0.5; for patient global assessment<10; and (2) no clinical deterioration. The last three columns of the table show the results of the study for patients experiencing at least one flare during the study.

The results indicate that the magnitude of the response to DHEA treatment increased with the severity of disease (i.e., from the less severe "active SLE" category to the "more severe" category to the "SLE" category in which patients were receiving corticosteroids and/or immunosuppressives). In addition, DHEA treatment reduced the occurrence of flares, and the magnitude of this effect also increased with the severity of disease.

The results of this trial are also shown in FIG. 1, which is a graph of the percentage of patients who did not experience a flare over the indicated duration of the study. FIG. 1 demonstrates that DHEA treatment reduces the risk of flare in "active SLE" patients, as compared to the placebo group, beginning at about 85 days of treatment. At about 200 days of treatment, incidence of flare is at least about 5% lower in the treated patients, and from this point on, the difference in flare incidence between the treated and placebo patients grows to at least about 10%.

TABLE 8

PERCENT RESPONDERS* AND PATIENTS WITH
AT LEAST ONE DEFINITE FLARE

| VARIABLE | RESPONDERS* | | | PATIENTS WITH AT LEAST ONE FLARE | | |
|---|---|---|---|---|---|---|
| Population | Placebo | DHEA | P Value† | Placebo | DHEA | P value† |
| Per Protocol‡ | 45% (80/176) | 58% (99/170) | 0.018§ | 27% (47/176) | 22% (37/170) | 0.335 |
| Active SLE‖ | 49% (65/133) | 66% (87/132) | 0.005 | 31% (41/133) | 24% (31/132) | 0.201 |
| More Severe SLE¶ | 44% (37/85) | 64% (51/80) | 0.010 | 39% (33/85) | 26% (21/80) | 0.056 |

*A responder is defined as a patient who satisfies the following conditions: (1) Weighted average change from baseline for Systemic Lupus Activity Measure (SLAM) < 1; for Systemic Lupus Erythematosus Disease Activity Index (SLEDAI) < 0.5; for Krupp Fatigue Severity Scale (KFSS) < 0.5; for patient global assessment < 10; and (2) no clinical deterioration.
†P-value for responder is from a logistic regression analysis with treatment as a factor; P-value for flare is from a log-rank test for time to first definite flare.
‡On study drug for > 60 days, had measurements of SLE scores or other data (pertinent to flare determination and clinical deterioration) beyond 60 days), and had no major protocol violations.
§A significant treatment interaction with baseline SLEDAI (baseline SLEDAI > 2 and ≦ 2) was noted, p = 0.0003. Therefore, patients with baseline SLEDAI 0–2 should not be pooled with those with baseline SLEDAI > 2 to determine treatment effect.
‖Per-protocol patients with SLEDAI > 2 at baseline.
¶Per-protocol patients with SLEDAI > 2 and receiving corticosteroids and/or immunosuppressives at baseline Thus, in accordance with one aspect of the invention, DHEA treatment can substantially reduce the risk of flare, especially in patients with a SLEDAI value greater than 2.0.

III. Treatment Method

The invention provides a method for treating SLE in an individual. The individual can be any animal that has SLE or an SLE-like condition. Generally, the individual is a mammal, and preferably a human SLE patient. Preferably, the individual has a SLEDAI value of greater than 2.0. According to the method, DHEA is administered to the individual and then the four disease-activity and constitutional symptom variables discussed above (SLEDAI, KFSS, VAS, AND SLAM) are determined and compared to baseline values determined before initiating DHEA administration. A decrease in three of these four variables and either a decrease, no change, or an increase of no more that about 5% of a baseline value in the fourth variable indicates that the individual is responding to said DHEA administration.

A. DHEA

In the SLE treatment method of the invention, an effective amount of a pharmaceutically active form of dehydroepiandrosterone ("DHEA") is administered to an individual with SLE. As used herein, the term "pharmaceutically active form of DHEA" includes pharmaceutically active acid, salt, and ester forms of DHEA, such as DHEA sulfate (7alpha-3H-DHEA sulfate, e.g., Heinz).

DHEA can be isolated in at least 6 different polymorphic forms, as described in detail in co-owned PCT Application No. PCT/US/00/06987 (International Publication No. WO 00/54763). DHEA was previously known, via analytical techniques such as x-ray diffraction, infrared (IR) spectroscopy, and differential scanning calorimetry (DSC), to occur in several different hydrate and anhydrate crystal forms. The anhydrate forms include forms I, II, IWII IV and V, although the latter two forms have been observed only transiently by DSC. The hydrates (solvates) include forms S1 (¼ hydrate), S2 (monohydrate), S3 (monohydrate), and S4 (½ methanolate). PCT Application No. PCT/US/00/06987 describes an additional form, form VI, which is detectable only by solid state NMR.

In preferred embodiments of the present invention, the DHEA employed has defined bioavailabilities and pharmacokinetic properties, which can be achieved by using preparations containing polymorphs that provide the desired properties.

In one aspect, the treatment method employs a DHEA preparation that is at least about 85%, preferably at least about 90%, more preferably at least about 95%, and most preferably at least about 99% form I. The form I polymorph has the following characteristics:

(1) X-Ray Powder Diffraction unique peaks at 15.0 (s), 16.8 (w), 18.0 (m), 18.7 (m), 19.1 (w), 19.3 (w), 20.2 (w), 24.8 (w) 25.0 (w), 25.2 (w) (peak positions are given in degrees 2θ; s=strong, m=medium, w=weak); and (2) Solid State 13C-NMR peaks: 14.8, 14.1 ppm carbon no. 18, 120.4, 118.9 ppm carbon no. 6, where these characteristics are measured as described in PCT Application No. PCT/US/00/06987.

DHEA form I-containing preparations exhibit good uptake by the GI tract upon oral administration, show good therapeutic activity, and are highly stable under ambient conditions.

In another aspect, the DHEA preparation is at least about 85%, preferably at least about 90%, more preferably at least about 95%, and most preferably at least about 99% form II. The form R polymorph has the following characteristics:

(1) X-Ray Powder Diffraction unique peaks at 8.6 (w), 17.3 (w), 20.9 (m), 22.0 (w), 22.2 (w), 27.1 (w) (peak positions are given in degrees 2θ; s=strong, m=medium, w=weak); and (2) Solid State 13C-NMR peaks: 13.1 ppm carbon no. 18, 119.9 ppm carbon no. 6, where these characteristics are measured as described in PCT Application No. PCT/US/00/06987.

DHEA form II-containing preparations exhibit good uptake by the GI tract upon oral administration, a rapid rate of absorption (greater than the form I polymorph) and good therapeutic activity, and are also stable under ambient conditions.

Additionally, DHEA preparations useful in the treatment method can contain mixtures of the form I and II polymorphs. Generally, the combined form I and II polymorphs account for at least about 85%, preferably at least about 90%, more preferably at least about 95%, and most preferably at least about 99% of the DHEA in such preparations. Preparations enriched in form I and/or form II, as described herein, provide more predictable pharmacokinetic profiles than are provided by compositions having random polymorphic compositions.

Such compositions, including DHEA, and precursors such as DHEA acetate, are commercially available from various sources (e.g., Sigma Chemical Co., St. Louis, Mo.; Aldrich Chemical Company, Inc.; Diosynth, Inc.; Pfaltz & Bauer, Inc.; Schering AG). DHEA compositions enriched for selected polymorphs can be prepared by crystallization of commercial DHEA in selected solvents under appropriate cooling or evaporation conditions.

In one preferred method, pure form I is prepared by (a) crystallizing DHEA from anhydrous 2-propanol (or, alternatively, acetone or acetonitrile) under a nitrogen stream at room temperature over about 2 days, producing a crystalline precipitate that contains predominantly form I and some amount of form VI, followed by (b) suspending the precipitate in ethyl acetate (about 100 mL/30 g of DHEA) and stiring the resulting slurry at room temperature for about one week, followed by filtration. The filter cake is allowed to dry at room temperature overnight. 13C-SSNMR analysis (discussed below) showed that product prepared by this method consisted of pure or nearly pure (>99%) form I; no other forms were detected by 13C-SSNMR.

DHEA highly enriched for form II can be obtained by rapid crystallization from tetrahydrofuran (THF), dioxane, chloroform or mixtures of chloroform and THF. Example 1 of PCT Application No. PCT/US/00/06987 provides a specific procedure for crystallization from THF, which produced a product shown by X-ray powder diffraction to be pure form II.

B. Formulation and Administration of DHEA

DHEA may be administered in a variety of ways, orally, including orally, parenterally, transcutaneously, transmucosally, or by inhalation, although oral administration is generally preferred.

Depending upon the manner of introduction, the DHEA may be formulated in a variety of ways. DHEA formulations can be prepared in various pharmaceutical forms, such as granules, tablets, capsules, suppositories, powders, controlled release formulations, suspensions, emulsions, creams, ointments, salves, lotions, or aerosols and the like. Preferably, DHEA formulations are employed in solid dosage forms suitable for simple, and preferably oral, administration of precise dosages. Solid dosage forms for oral administration are preferably tablets, capsules, or the like.

DHEA formulations useful in the invention can include one or more pharmaceutical grade organic or inorganic carriers, excipients, and/or diluents, especially those suitable for oral or topical use. Such carriers include tocopherol, dimethyl sulfoxide, and the like. For oral administration, suitable excipients include lactose, mannitol, starch, magnesium stearate, sodium saccharine, talcum, cellulose, glucose, gelatin, sucrose, magnesium carbonate, and the like.

To prepare orally deliverable tablets, DHEA is mixed with at least one pharmaceutical excipient, and the solid formulation is compressed to form a tablet according to known methods, for delivery to the gastrointestinal tract. The tablet composition is typically formulated with additives, e.g. a saccharide or cellulose carrier, a binder such as starch paste or methyl cellulose, a filler, a disintegrator, or other additives typically usually used in the manufacture of medical preparations. To prepare orally deliverable capsules, DHEA is mixed with at least one pharmaceutical excipient, and the solid formulation is placed in a capsular container suitable for delivery to the gastrointestinal tract.

Diluents known in the art include, for example, vegetable and animal oils and fats. Stabilizing agents, wetting and emulsifying agents, salts for varying the osmotic pressure, buffers for securing an adequate pH value, and/or skin penetration enhancers can be used as auxiliary agents in the DHEA formulations. Methods for preparing various conventional dosage forms are known or will be apparent to those skilled in the art; for example, see *Remington's Pharmaceutical Sciences* (19th Ed., Williams & Wilkins, 1995).

The proportion of pharmaceutically active DHEA to carrier and/or other substances may vary from about 0.5 to about 100 wt.% (weight percent). For oral use, the pharmaceutical formulation will generally contain from about 5 to about 100% by weight of the active material. For other uses, the formulation will generally have from about 0.5 to about 50 wt.% of the active material.

DHEA formulations employed in the invention provide an effective amount of DHEA upon administration to an individual. As used in this context, an "effective amount" of DHEA is an amount that is effective to ameliorate a symptom of SLE. Such a therapeutic effect is generally observed within about 4 to about 6 weeks of initiating administration of an effective amount of DHEA.

The subject formulations are preferably, though not necessarily administered daily, in an amount to provide at least about a 10%, and more usually at least about 25%, increase in the blood level of DHEA. Generally, the total daily dosage will be at least about 50 mg, preferably at least about 100 mg, and more preferably at least about 200 mg, and preferably not more than 500 mg per day, administered orally, e.g., in 4 capsules or tablets, each containing 50 mg DHEA. Although capsules or tablets for oral delivery can conveniently contain up to a full daily oral dose, e.g., 200 mg or more. Where administration by other than an oral route, the DHEA may be delivered over an extended period, e.g., 3–10 days, in an amount effective to produce at least an average daily dose of, e.g., 50 mg.

DHEA treatment is carried out for an extended period, typically at least about 20, at least about 40, or at least about 60 weeks, and preferably as long as the patient is receiving noticeable benefit from the treatment method.

In preferred embodiments, DHEA is administered at a dose and for a period effective to produce a decrease in three of the four disease-activity and constitutional-symptom variables characterizing an individual's SLE condition and either a decrease, no change, or an increase of no more that about 3% of a pretreatment baseline value in the fourth variable. Preferably, the DHEA is administered at a dose effective to reduce the risk that an individual will experience an SLE flare at about 200 days of DHEA administration by at least about 5%. The risk of an SLE flare is said to be reduced by at least about 5% if at 200 days of DHEA treatment, the incidence of flare is at least about 5% lower in a DHEA-treated population, as compared to a placebo-treated population. The relevant populations are those in which the severity of disease is matched to the subject individual, i.e., the reduction in risk that an individual will experience a flare is defined in terms of DHEA- and placebo-treated populations that have the same severity of disease as the individual. For this purpose, the severity of disease is the same if the individual and two populations fall into one of the population groups identified in Table 8 above.

DHEA treatment can be combined with administration of one or more other drugs that are used in accordance with conventional SLE treatments, which include corticosteroids, such as glucocorticoids; non-steroidal anti-inflammatory agents; immunosuppressants; and anti-malarials. examples of such drugs include hydroxychloroquine, prednisone, quinacrine, azathioprine, and immunosuppressants, such as anticytokines, including anti-TNF-2, TNF-2 receptor antagonists, anti-IL-1, anti-IL-6, and anti-CD40 ligand. Dosages for the glucocorticoid prednisone, for example, are generally from about 1-15, more usually from about 1-12 mg/day, and typically more than 2 mg per day. The additional drugs may be administered separately or in conjunction with DHEA and may, if desired, be formulated in the same formulation with DHEA.

IV. Pharmaceutical Product

The invention also provides a pharmaceutical product for use in treating SLE in an individual including a plurality of doses of a pharmaceutically active form of DHEA, and instructions for performing the treatment method of the invention. Specifically, the instructions direct that:

1) an effective amount of a pharmaceutically active form of DHEA be administered to an individual with SLE;

2) the following disease-activity and constitutional-symptom variables characterizing the individual's SLE condition be determined: SLEDAI, KFSS, VAS, and SLAM at least about after initiating DHEA administration; and 3) the differences between the values for SLEDAI, KFSS, VAS, and SLAM after initiating DHEA administration and baseline values for SLEDAI, KFSS, VAS, and SLAM before initiating DHEA administration be determined, wherein a decrease in three of these four variables and either a decrease, no change, or an increase of no more that about 5% of a baseline value in the fourth variable indicates that the individual is responding to said DHEA administration.

The pharmaceutically active DHEA can be formulated as described above with reference to the treatment method of the invention and can be packaged in any convenient manner.

Generally, the instructions direct the administration of DHEA as described above with reference to the treatment method. Oral administration is preferred. In a preferred embodiment, the instructions specify selecting those individuals having a SLEDAI value greater than 2.0 for DHEA administration.

The instructions can be affixed to the packaging material or can be included as a package insert. While the instructions typically comprise written or printed materials they are not limited to such. Any medium capable of storing such instructions and communicating them to an end user is contemplated by this invention. Such media include, but are not limited to, electronic storage media (e.g., magnetic discs, tapes, cartridges, chips), optical media (e.g., CD ROM), and the like. As used herein, the term "instructions" can include the address of an internet site that provides the instructions.

The invention also includes the use of the above-described pharmaceutical product for the treatment of SLE in a human patient.

All publications and patents cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the scope of the appended claims.

What is claimed is:

1. A method for determining whether an individual with systemic lupus erythematosus (SLE) is responding to DHEA administration for treatment of SLE, comprising:

a) at least about 4 weeks after initiating DHEA administration, determining the following, disease-activity and constitutional-symptom variables characterizing the individual's SLE condition: the SLE Disease Activity Index (SLEDAI), Krupp Fatigue Severity Score (KFSS), the Patient Visual Analog Scale (Patient VAS), and the Systemic Lupus Activity Measurement (SLAM); and b) determining the differences between the values for SLEDAI, KFSS, VAS, and SLAM after initiating DHEA administration and baseline values for SLEDAI, KFSS, VAS, and SLAM before initiating DHEA administration, wherein a decrease in three of these four variables and either a decrease, no change, or an increase of no more than about 5% of a baseline value in the fourth variable indicates that the individual is responding to said DHEA administration.

2. The method of claim 1, wherein the individual is a human SLE patient.

3. The method of claim 2, wherein the method additionally comprises selecting those SLE patients having a SLEDAI value greater than 2 for said DHEA administration.

4. The method of claim 3, wherein at least about 85% of the DHEA administered is present as the form I polymorph, the form II polymorph, or a combination thereof.

5. The method of claim 4, wherein as least about 95% of the DHEA administered is present as the form I polymorph, the form II polymorph, or a combination thereof.

6. The method of claim 5, wherein as least about 95% of the DHEA administered is present as the form I polymorph.

7. The method of claim 5, wherein at least about 95% of the DHJEA administered is present as the form II polymorph.

8. The method of claim 3, wherein the administration of DHEA produces a decrease in three of the four disease-activity and constitutional-symptom variables characterizing an individual's SLE condition. and either a decrease, no change, or increase of no more than about 3% of a pretreatment baseline value in the fourth variable.

9. The method of claim 3, additionally comprising determining the incidence of SLE flare over at least about 200 days of DHEA administration.

10. The method of claim 3, wherein said DHEA administration comprises administering a daily oral dose of at least about 100 mg of a pharmaceutically active DHEA to the SLE patient.

11. The method of claim 10, wherein the dose is at least about 200 mg DHEA/day, for a period of at least about 40 weeks.

12. The method of claim 10, wherein the SLE patient is receiving an orally administered drug selected from the group consisting of: a glucocorticoid, a non-steroidal anti-inflammatory agent, an immunosuppressant, and an anti-malarial drug prior to administration of DHEA, and said method includes continuing administration of said drug during the period of DHEA administration.

13. The method of claim 12, wherein said drug is prednisone, at a daily dose of at least 2 mg.

14. The method of claim 1, wherein a treatment regimen, comprising said DHEA administration, produces an improvement in the individual's SLE condition, as determined by a decrease in three of said four variables and either a decrease, no change, or an increase of no more than about 5% of a baseline value in the fouth variable, and the treatment regimen is continued.

15. The method of claim 14, wherein the treatment regimen is continued for at least about 20 weeks.

16. The method of claim 15, wherein the treatment regimen is continued for as long as said improvement is achieved.

* * * * *